(12) United States Patent
Cuddihy et al.

(10) Patent No.: US 7,091,865 B2
(45) Date of Patent: Aug. 15, 2006

(54) SYSTEM AND METHOD FOR DETERMINING PERIODS OF INTEREST IN HOME OF PERSONS LIVING INDEPENDENTLY

(75) Inventors: Paul Edward Cuddihy, Ballston Lake, NY (US); Jenny Marie Weisenberg, Schenectady, NY (US); Meena Ganesh, Clifton Park, NY (US); Catherine Mary Graichen, Malta, NY (US)

(73) Assignee: General Electric Company, Niskayuna, NY (US)

( * ) Notice: Subject to any disclaimer, the term of this patent is extended or adjusted under 35 U.S.C. 154(b) by 260 days.

(21) Appl. No.: 10/772,761

(22) Filed: Feb. 4, 2004

(65) Prior Publication Data

US 2005/0181771 A1    Aug. 18, 2005

(51) Int. Cl.
*G08B 23/00* (2006.01)
(52) U.S. Cl. .............................. 340/573.1; 340/539.11; 340/539.14; 340/539.16; 340/539.22; 340/545.1; 340/545.6
(58) Field of Classification Search ............. 340/573.1, 340/573.4, 545.1, 545.6, 539.1, 539.11–539.14, 340/539.16–539.17, 539.22, 309.16; 379/38
See application file for complete search history.

(56) References Cited

U.S. PATENT DOCUMENTS

| | | | | |
|---|---|---|---|---|
| 3,885,235 A | * | 5/1975 | Bergstrom et al. ........ | 340/573.1 |
| 4,064,368 A | * | 12/1977 | Dibner ...................... | 379/38 |
| 4,259,548 A | * | 3/1981 | Fahey et al. ................ | 379/38 |
| 4,524,243 A | * | 6/1985 | Shapiro ................... | 340/573.1 |
| 4,743,892 A | * | 5/1988 | Zayle ...................... | 340/573.4 |
| 4,990,893 A | * | 2/1991 | Kiluk ...................... | 340/573.1 |
| 5,692,215 A | | 11/1997 | Kutzik et al. | |
| 6,108,685 A | | 8/2000 | Kutzik et al. | |
| 6,540,674 B1 | | 4/2003 | Zadrozny et al. | |
| 2002/0171551 A1 | | 11/2002 | Eshelman et al. | |
| 2004/0030531 A1 | | 2/2004 | Miller et al. | |

FOREIGN PATENT DOCUMENTS

CA    2208594    12/1994

* cited by examiner

*Primary Examiner*—Thomas Mullen
(74) *Attorney, Agent, or Firm*—Jean K. Testa; Donald S. Ingraham (57) ABSTRACT

A system and method for monitoring the activities of a resident living independently to distinguish normal activity from unusual activity. A variety of sensors distributed around the home collect data on activity in the home. The data is communicated to a remote monitoring center and collated in a database according to applicable time slots. The time slots for a twenty-four hour cycle are at least three and can be as many as forty-eight or more. Historical activity time lines are created and a buffer time is added to and offset from the maximum historical activity time line. If a new data point comes in that exceeds both the maximum historical activity time line and the buffer time, an alert is issued indicating the activity is unusual.

42 Claims, 5 Drawing Sheets

SYSTEM AND METHOD FOR DETERMINING PERIODS OF INTEREST IN HOME OF PERSONS LIVING INDEPENDENTLY

BACKGROUND

The invention relates generally to a system and a method for monitoring the in-home activities of persons living independently. More particularly, the invention relates to a system and a method for determining whether the activities of persons living independently are of interest as being unusual or whether the activities are normal.

With medical advancements and increased attention to proper nutrition and sufficient exercise, the populace in the western civilization is living longer. For example, the number of elderly persons residing in the United States is increasing, and with the advancing age of the baby boomer generation, the number of elderly persons in the United States will increase significantly over the next several decades. Additionally, increased awareness and understanding of various mental and physical disabilities has led to an increase in the number of persons having diminished mental and/or physical faculties living independently.

With the increase in elderly and disabled persons living independently has come anxiety that these elderly and disabled persons are safe and secure in their own residences. There is increased anxiety by the elderly and disabled living alone that they may become injured or incapacitated and be unable to summon assistance. That anxiety is often shared by loved ones living at a distance from the elderly and/or disabled living independently.

Currently, the anxiety felt by the elderly and disabled living alone, as well as the anxiety felt by their loved ones, is addressed through several avenues. One way to ease anxiety is through frequent visits to the home by a caregiver. Such visits can be intrusive, time consuming, and often inconvenient and not appreciated. Another way is for the elderly or disabled person to move out of the home and move into a facility better able to monitor his health. This, however, strips the person of his independence, is costly and is often unwelcome. Another way is through technological assistance or monitoring of the person in the home.

Such technological systems that assist persons in their home include Personal Emergency Response Systems. In these systems the elderly or disabled individual wears a watch, pendant or other like device and presses a button in the event of an emergency, such as a fall. The depressed button enables an alarm signal. A central monitoring facility provides assistance by responding to the alarm signal and calls the individual to identify the problem. The facility can also call a predetermined list of contacts, such as relatives, neighbors or emergency services, as required by the context of the situation. While a valuable service, these systems only identify problems that occur when the individual is able to press the emergency button.

Some known in-home monitoring systems attempt to detect unusual activity, such as, for example, an abnormally long quiet period within the house, by arbitrarily choosing "daytime" and "nighttime" parameters and sending an alert if there is no activity for at least five hours during the "daytime" time period. These known in-home monitoring systems provide the resident with a button which can be pressed to indicate whether the resident is home or is away. Such known systems oftentimes fail to accurately reflect real daytime and nighttime patterns of the resident. Further, the resident's responsibility to indicate whether he is in the house or away often goes unfulfilled, leading to a high false alert rate and low sensitivity for such known systems.

Thus, there remains a need for a system and method for ascertaining whether the in-home activities of a person living independently are within the norm for such a person or whether they are unusual or irregular.

SUMMARY

The invention is directed to a system and a method for ascertaining appropriate active and inactive time periods for a particular household. The system is capable of monitoring the activity level in a house and alerting a caregiver when an unusual period of activity, or inactivity, is determined.

One aspect of the invention is system for monitoring activity of a resident. The system includes at least one sensor for collecting data points on activity of the resident, a communication platform in communication with the at least one sensor, and a monitoring center located remote from the resident and in communication with the communication platform. The monitoring center includes a database for collecting the data points on activity of the resident. The collected data points are collated into at least three time slots per every twenty-four hour time cycle for determining activity of the resident.

Another aspect of the invention is a system for monitoring activity within a home. The system includes a plurality of sensors positioned throughout the home for collecting data points on activity in the home, a communication platform in communication with the plurality of sensors, and a monitoring center located remote from the home and in communication with the communication platform. The plurality of sensors includes one or more motion sensors, exterior door sensors, inside door sensors, cabinet sensors, kitchen sensors, appliance sensors, hazard sensors, and security sensors. The monitoring center includes a database for collecting the data points on activity in the home. The collected data points are collated into at least ten time slots per every twenty-four hour time cycle for determining activity within the home.

Another aspect of the invention is a method for distinguishing between normal and unusual activity in a home. The method includes the steps of obtaining historical activity data within the home for a twenty-four hour cycle, collating the historical activity data into at least three time slots within the twenty-four hour cycle, and evaluating a new data point against the collated historical activity data to determine whether the new data point indicates normal or unusual activity in the home.

Another aspect of the invention is a method for distinguishing between unusual periods of inactivity and normal periods of inactivity in a home. The method includes the steps of obtaining historical activity data within the home for a twenty-four hour cycle, collating the historical activity data into at least ten time slots within the twenty-four hour cycle, producing a maximum historical inactivity time line based upon the collated historical activity data, and evaluating a new data point against the collated historical activity data to determine whether the new data point indicates an unusual period of inactivity or a normal period of inactivity in the home.

These and other advantages and features will be more readily understood from the following detailed description of preferred embodiments of the invention that is provided in connection with the accompanying drawings.

DETAILED DESCRIPTION OF PREFERRED EMBODIMENTS

Figure 1:
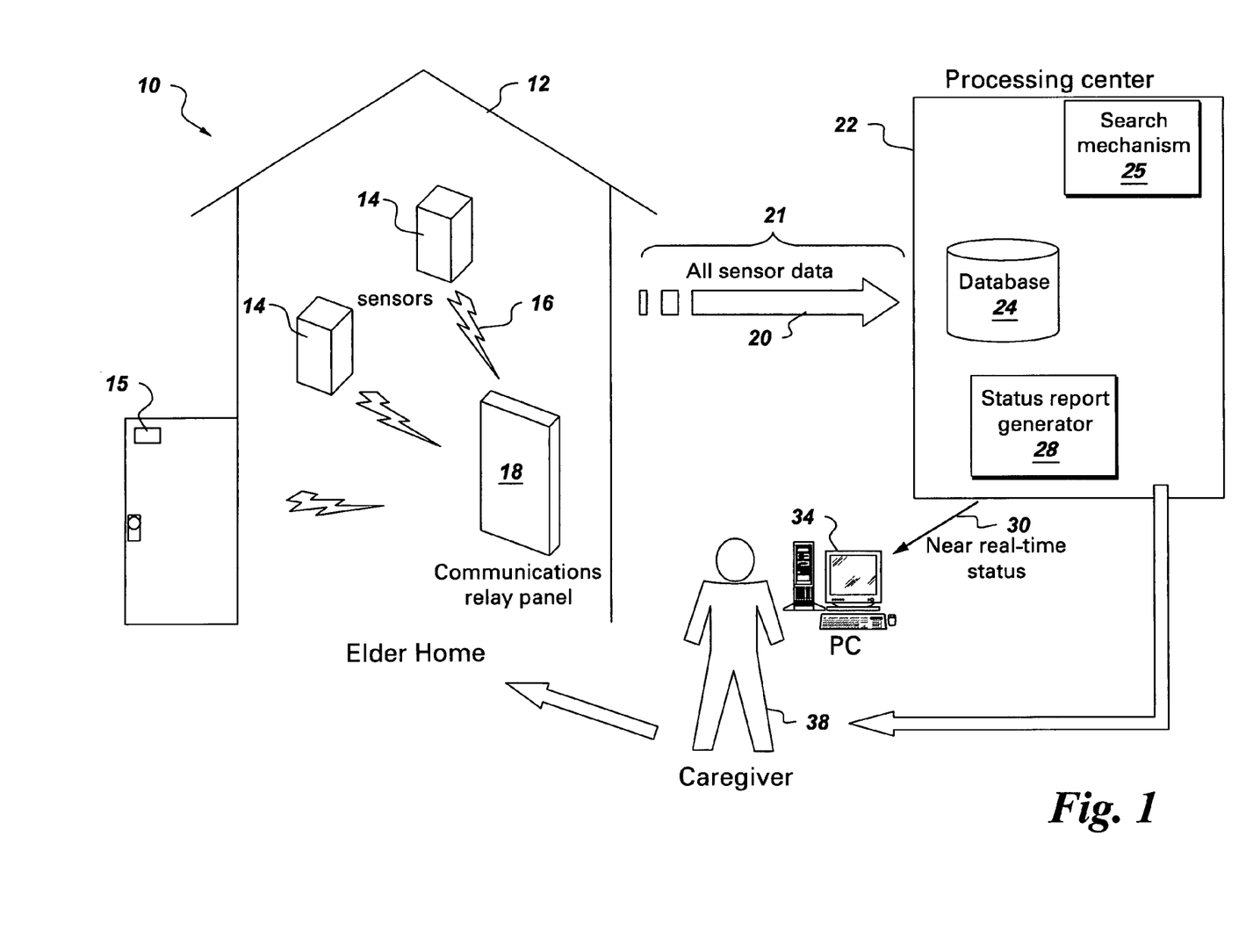
FIG. 1 is a schematic view of a remote in-home monitoring system in accordance with an exemplary embodiment of the invention.

With reference to FIG. 1, there is shown an activity monitoring system 10 that includes activity sensors 14, exterior door sensors 15, a communication relay panel 18, and a remote monitoring center 22. The activity monitoring system 10 lacks mechanisms to intervene in the home 12 or any subsystems (appliances, water, lights, etc.) of the home 12. Intervention in the home 12, if any, may arrive through a communication with the resident of the home 12 from outside the home, such as via a telephone call or a visit from a caregiver 38 or other suitable person, such as an emergency response professional. Further, a speakerphone may be included in the system 10 that communicates with a central monitoring station to allow a resident to request assistance after pressing an old-fashioned panic button. The sensors 14 include motion sensors, inside door sensors, cabinet sensors, kitchen and appliance sensors, and any other sensors suitable for collecting and communicating data regarding activities on-going in the home 12. Other suitable sensors 14 include hazard sensors and security sensors. The exterior door sensors 15 may be one or more sensors positioned on doors providing ingress and egress from the home 12. Preferably, the sensors 14, 15 are wireless sensors capable of wirelessly communicating signals 16, which include data collected, to the communications relay panel 18. It should be appreciated, however, that the sensors 14 instead may be sensors hardwired to the communications relay panel 18.

The communications relay panel 18 communicates the sensor data, or data points, 19 collected from the sensors 14, 15 by sending a data signal 20 containing the data points 19 to the remote monitoring center 22 by way of a suitable wired or wireless communications platform 21, such as, for example, wired telephone, wireless telephone, two-way walkie-talkie, pager, cable, the Internet, or any other wireless communication platform. Depending upon the communication platform 21 chosen, the data signals 20 may be sent in near real-time or may be sent at discrete, irregular intervals. For example, data signals 20 may be sent in near real-time via wireless telephone, two-way walkie-talkie, pager, cable, the Internet or any other wireless communication platform. For a wired telephone communication platform, the data signals 20 are buffered and transmitted at differing intervals.

The monitoring center 22, which is remote from the home 12, includes a database 24, and a status report generator 28. The database 24 serves as a collection vessel for the sensor data communicated via the signals 20. Upon a request from the caregiver 38 for a status report, the sensor data is forwarded from the database 24 to the status report generator 28. The status report generator 28 communicates a near real-time status signal 30 to a personal computer 34 of the caregiver 38. By near real-time is meant anywhere in the range of almost instantaneously to up to three minutes. For example, for a two-way page communication platform 21, the amount of time required for the communication can be between two and three minutes. The status report generator 28 may be programmed to update the report for each home 12 at a certain interval, such as, for example, every ten minutes. The status signal 30 includes a report generated by the status report generator 28. The format and substance of the report are dependent upon the request of the caregiver 38. It should be appreciated that the signal 30 can instead be communicated via a personal digital assistant (PDA), a pager, a facsimile machine, cable, or a telephone or voice-mail account instead of via the personal computer 34.

The sensors 14, 15 can be positioned in various locations throughout the home 12. The sensors 14, 15 may be categorized by types, for example, as motion, exterior door (sensor 15), food, or automobile sensors. It should be appreciated that the number of sensors 14, 15 used may depend upon the layout of the home 12, as well as other factors.

Next, with specific reference to FIGS. 1–3 and 5, will be described a process for determining whether a particular activity is considered unusual in a specific home 12. One type of activity for review is the distribution of inactivity throughout a twenty-four hour cycle. For example, an accumulated amount of inactivity during a period of time in which the sensors 14, 15 of a specific home 12 normally detect activity may be considered unusual and may be an indication of a problem within the home 12. The first step in the process, Step 200 (FIG. 5), is to obtain historical data points 19 of activity detected by the sensors 14, 15 within a home 12. Each historical data point indicates the length of time the home has been quiet at a given point in time. Table 1 provides some sample historical data points 19. Data points 19 can be collected by the sensors 14, 15 at any interval that is suitable to provide relatively quick response should a problem be detected in the home 12. One preferred interval is data collection every thirty minutes; however, the data collection could be at intervals of every fifteen minutes or less to every hour or more. The historical data points, as shown in Table 1, are computed from the raw data points 19 transmitted in the data signal 20 to the monitoring center 22.

TABLE 1

| Date | Time slots (TS) | | | | | |
|---|---|---|---|---|---|---|
| | 00:00 | ... | 9:00 | 9:30 | 10:00 | ... | 23:30 |
| Dec. 01, 2003 | 96 | ... | 0 | 30 | 3 | ... | 42 |
| Dec. 02, 2003 | 72 | ... | 2 | 6 | 8 | ... | −1 |
| Dec. 03, 2003 | −1 | ... | 44 | 74 | 6 | ... | 45 |

Figure 2:
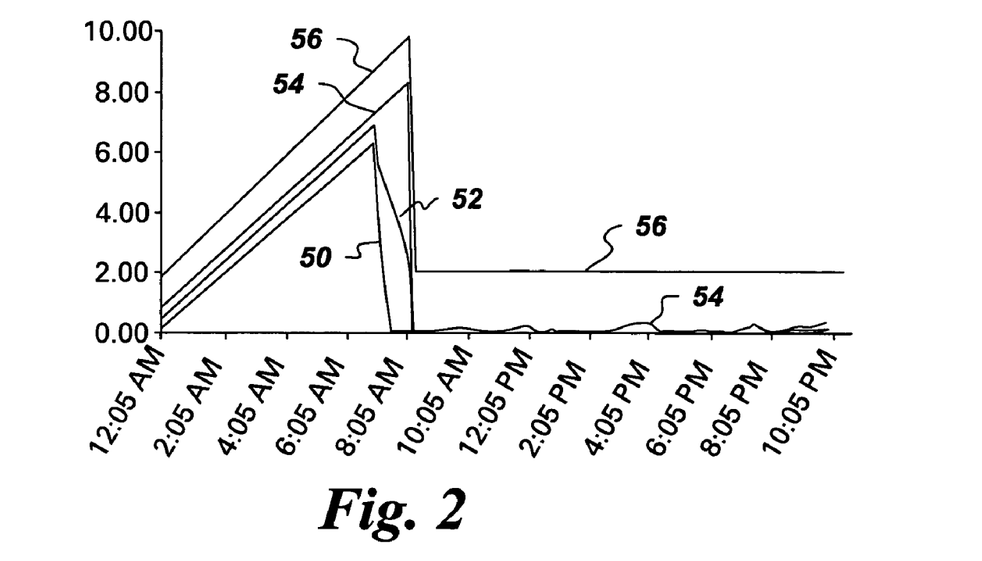
FIG. 2 is a graph illustrating average, minimum and maximum quiet data from a ten day period of data collection using the remote in-home monitoring system of FIG. 1.

For any given time slot, and as indicated in Table 1 the time slots are at thirty minute intervals, if the home 12 has been inactive for longer than the maximum inactive time according to the historical data points 19 for the same time slot, then it can be presumed that the resident has been quiet (inactive) for longer than ever before during that time slot. For Table 1, on December 1, as of 12 AM (00:00), there had been 96 minutes of quiet, whereas on December 2, there had been 72 minutes of quiet. The presence of a −1 signifies that the resident was not at home during that time period. The historical data points 19 can then be amassed and formulated into time lines indicating maximum, average, and minimum activities per time slot. FIG. 2 shows a sample minimum inactivity time line 50, average inactivity time line 52, and maximum inactivity time line 54.

At Step 205 (FIG. 5), a buffer time period is added to the maximum historical quiet time embodied in the maximum inactivity time line 54 of FIG. 2. The rationale for providing a buffer is that inactivity for a short amount of time longer than has been registered in the past may not be appropriate for the issuing of an alert. With reference to FIG. 2, as one may expect, the greatest accumulation of inactivity, slightly in excess of eight hours, is at about 8:00 AM. Further as one may expect, the accumulation of inactivity follows an upwardly sloping curve from around midnight to the 8:00 AM time slot, at which point the slope sharply descends. A buffer, or alert, timeline 56 is provided at an interval of ninety minutes above the maximum inactivity timeline 54. In this way, an alert is delayed ninety minutes from any anomalous data point 19 during any time slot. For example and with reference to the data in Table 1, if a ninety-minute buffer is used, then at 9:30 the resident must be quiet for longer than seventy-four plus ninety minutes, or two hours and forty-four minutes, before an alert is issued. Further, it should be appreciated for timelines that represent inactivity, the maximum inactivity timeline 54 cannot increase more than the duration of the timeslot between two adjacent timeslots. For example, and with reference to Table 1, if the 00:00 value for Dec. 1, 2003 represents the maximum value of quiet time experienced, namely ninety-six minutes, and the timeslots are thirty minutes each, then the maximum valued at 12:30 AM (00:30) cannot be greater than one-hundred and twenty-six minutes.

Figure 3:
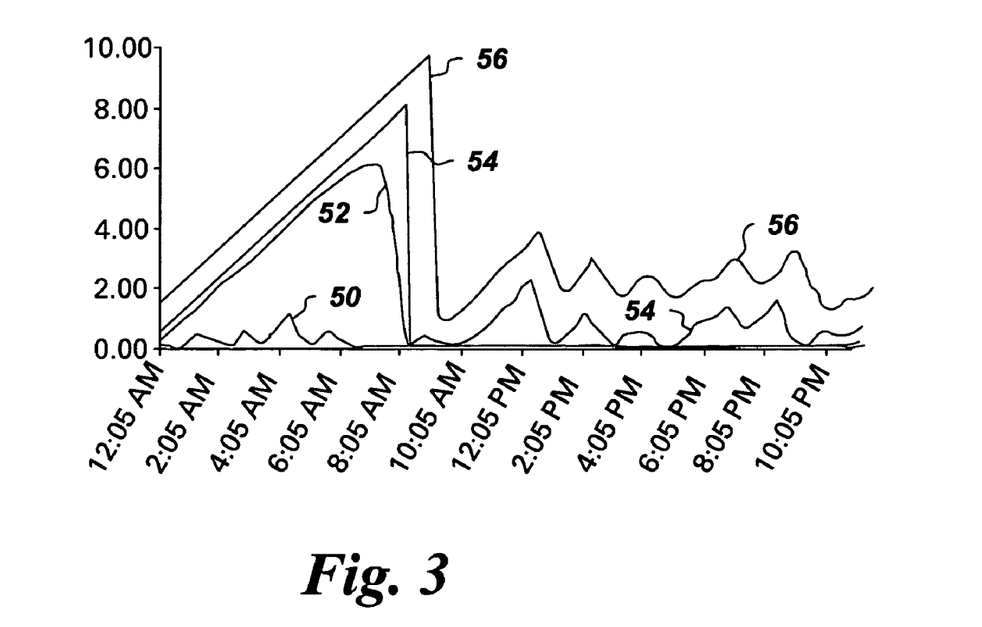
FIG. 3 is a graph illustrating average, minimum and maximum quiet data from a two month period of data collection using the remote in-home monitoring system of FIG. 1.

At Step 210, the buffer timeline 56 is offset. The rationale for offsetting the buffer timeline 56 is to allow for comparison of a particular time slot with surrounding time slots (for example, comparing the time slot 9:30 AM with the historical data for the time slot 9 AM). Taking the data points 19 in Table 1 as an example, the maximum amount of inactivity as of 9 AM is 44 minutes and the maximum amount of inactivity as of 9:30 AM is 74 minutes. If one assumes a buffer of ninety minutes for the timeslot currently in question (TS 0), which is 9:30 AM, and a buffer of sixty minutes for the previous timeslot (TS −1), namely 9:00 AM, then if on a subsequent date at 9:30 AM the current quiet time exceeds both 164 minutes (74 plus 90) and 104 (44 plus 60), then an unusual period of inactivity has occurred. The offset buffer timeline 56 is shown in FIG. 3, which depicts minimum, average and maximum inactivity timelines 50, 52, 54 taken from data points 19 collected over a two-month period.

To further explain the rationale for offsetting the buffer timeline 56, consider the case in which a home 12 resident usually wakes up at 7:55 AM. The activity signature will show a high amount of cumulative inactivity for the 7:30 AM time slot, and a low amount of cumulative inactivity for the 8:00 AM time slot. If one only considers TS 0 (8:00 AM), and one day the resident awakes at 8:05 AM, an alarm is issued since the current cumulative inactivity for 8:00 AM is high, instead of its historical low level. However, if one were instead to also consider TS −1 (7:30 AM), a high cumulative inactivity period is acceptable, and hence an alarm would not be issued. Thus, considering TS −1 provides additional buffering for when the maximum inactivity timeline 54 drops steeply. Similar benefits can be achieved by applying buffers to TS −2, TS +1, and TS+2. Further, the amount of buffer can be varied such that TS 0 is given the most weight and the most leeway, whereas surrounding time slot histories are given progressively less weight. A reasonable buffer configuration for TS −2, TS −1, TS 0, TS+1 and TS+2 may be, respectively, sixty minutes, seventy-five minutes, ninety minutes, seventy-five minutes, and sixty minutes.

It should be appreciated that the sensitivity of the system 10 for sending alert notifications or recognizing unusual lack of activity is determined by the settings of the buffer configuration. Lower values make the system 10 more sensitive, but also decrease the time required to determine an unusual lack of activity. Larger values allow more deviation from past experience before issuing an alert, but also result in more time elapsing before the alert is issued.

Figure 4:
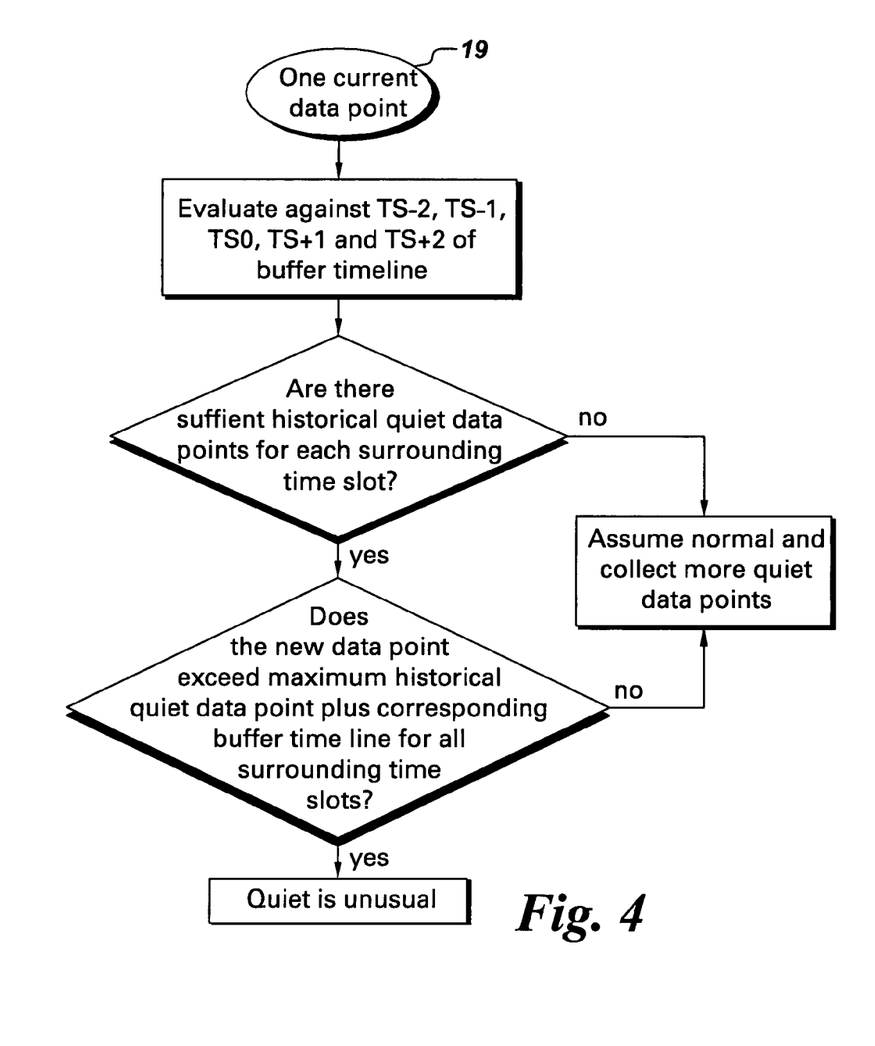
FIG. 4 illustrates a flow diagram for determining if a new quiet data point is normal or unusual activity.
Figure 5:
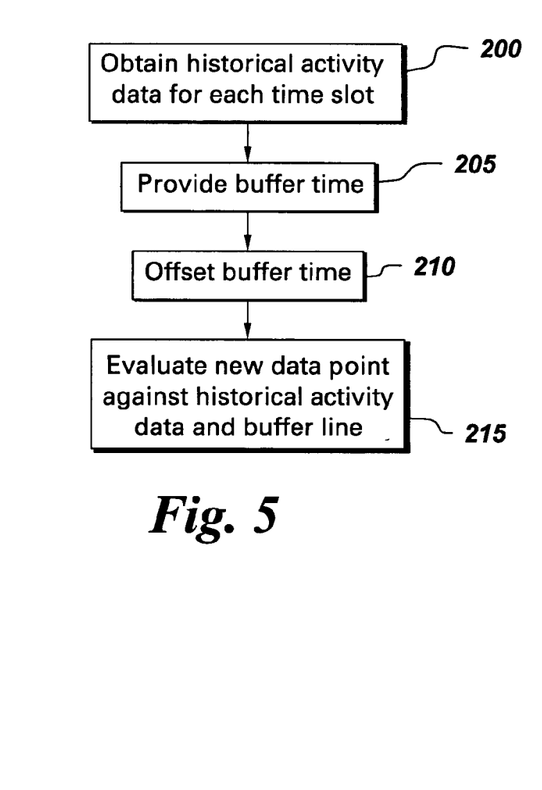
FIG. 5 illustrates process steps for determining whether a new data point from a sensor is an unusual data point.

Finally, at Step 215 (FIG. 5), a new data point 19 received at the monitoring center 22 from the sensors 14, 15 is evaluated against the buffer timeline 56 to determine whether it indicates usual or unusual inactivity. Referring specifically to FIG. 4, Step 215 is further described. As a current data point 19 is received from the sensors 14, 15, it is evaluated against the buffer timeline 56 at time slots TS −2, TS −1, TS 0, TS+1 and TS+2. Next, a determination is made whether there are sufficient historical data points 19 for each surrounding time slot. What is considered sufficient is, generally, no less than ten to twenty data points 19 for each time slot. If there are insufficient historical data points 19 for each surrounding time slot, it is assumed that the new data point 19 is normal and more data points 19 are collected. If there are sufficient historical data points 19, next is determined whether the new data point 19 exceeds both the maximum historical inactivity data point 19 and the corresponding buffer time line 56 for all the surrounding time slots. If the new data point 19 does not exceed the maximum historical inactivity data point 19 and the corresponding buffer time line 56 for all the surrounding time slots, it is considered normal and no alert is sent. If, on the other hand, the new data point 19 exceeds the maximum historical inactivity data point 19 and the corresponding buffer time line 56 for all the surrounding time slots, it is considered unusual, thus causing an alert to be sent.

Based upon the historical data collected for a home 12, the system 10 can create a database 24 of historical data that includes an automatically determined sleep window, a period during the twenty-four hour cycle during which average inactivity is at its highest. The buffer line 56 can be increased during the sleep window to lessen the chance that an alert is issued in the case of a resident sleeping better than he normally does. For example, a resident that gets up at generally the same time every night for a glass of water or to go to the bathroom would have a dip in the maximum accumulated inactivity during his sleep window. If one night the resident does not get up during the time period, an increase in the amount of buffer time would lessen the chance that an alert is issued in this case. The sleep window for a particular home 12 would be the part of the twenty-four hour cycle having the greatest area under the maximum inactivity time line 54. The sleep window is used as a filter. Buffer times are increased during the sleep window to assist in lessening alerts caused by a person sleeping with fewer interruptions than normal.

Alternatively, the evaluation of data, and any resulting follow-up activity based upon that evaluation, pertaining to the sleep window may instead be handled differently. For example, an alert for unusual inactivity during a sleep window may be delayed and sent after the sleep window period. Instead, the alert may be sent via e-mail instead of by phone.

Although described examples herein have focused on detecting unusual inactivity time periods, the same methodology can be used to detect other unusual events. For example, historical activity signatures for each subset of sensors (for example, motion, door, food, automobile) or for individual sensors (for example, refrigerator) can be constructed. Based upon the historical activity signatures thus constructed, unusual activity can be determined for subsets of sensors or for individual sensors. An example of the usefulness of such a strategy is the construction of activity signatures for kitchen sensors to enable detection of when a resident has gone too long without eating a meal.

Furthermore, instead of tracking the maximum inactivity threshold, historical activity signatures can be constructed based upon the minimum inactivity threshold. For example, the movement of an external door may be significant, depending upon the time at which such movement occurs. By taking historical data points 19 on the external doors with the sensors 15, historical data can be collected to provide a time line of activity. The time line will slope upwards during times of inactivity, generally during the night, and will slope sharply downward upon any movement. A data point 19 indicating the opening of an external door at, for example, 3:00 AM will be far below the minimum time line for the sensors 15, and my indicate an unusual occurrence.

One important aspect that underlies the process for collecting activity data for a home 12 is whether or not the resident is at home. Obviously, collecting data on inactivity in the home 12 when the resident is not at home will skew the historical data. For example, historically a resident wakes up at 8:00 AM. Thus, the historical time line would reflect a downward slope at about 8:00 AM, and may, for example, indicate a maximum inactivity time of eighteen minutes. If the resident sleeps late one morning (beyond both the maximum inactivity time line 54 and the buffer line 56), then an alert would issue. However, if the resident leaves the home 12 at noon on one day and stays away for two days, then if the resident's time away from the home 12 is counted as inactivity time, the activity signature would reflect a maximum elapsed inactivity time for 8:00 AM of over forty hours. Thus, the next time the resident awoke late, the activity signature would not indicate anything unusual.

The system 10 can provide information indicative of whether a resident is at home or away by utilizing the motion sensors 14 and the door sensors 15. For example, if a door sensor 15 is triggered and no subsequent triggering of any motion sensors 14 occurs within the home 12, an assumption can be drawn that the resident is not inside the home 12. Alternatively, if a door sensor 15 is triggered, and motion is thereafter sensed by the motion sensors 14, the assumption is that the resident is within the home 12. Data points 19 of inactivity collected while the resident is away from the home 12 are flagged in the historical database 24 since including such data points 19 will skew the results. Such flagged data is ignored for the purposes of constructing the buffer line 56, but counted for the purposes of determining if sufficient historical data exists.

It should be appreciated that there are other data points 19 that should be flagged and ignored as well. One example of a data point 19 that can be flagged and ignored is one that triggers the issuance of an alert. If a data point 19 that triggers an alert were included in the historical database 24, the database 24 would become less sensitive over time. Further, all data points 19 after a predetermined amount of time should be discarded as being stale. A preferred amount of time may be thirty to ninety days in the past. It should be appreciated, however, that the system 10 may still be useful with a historical database 24 extending backward only seven to ten days.

Figure 6:
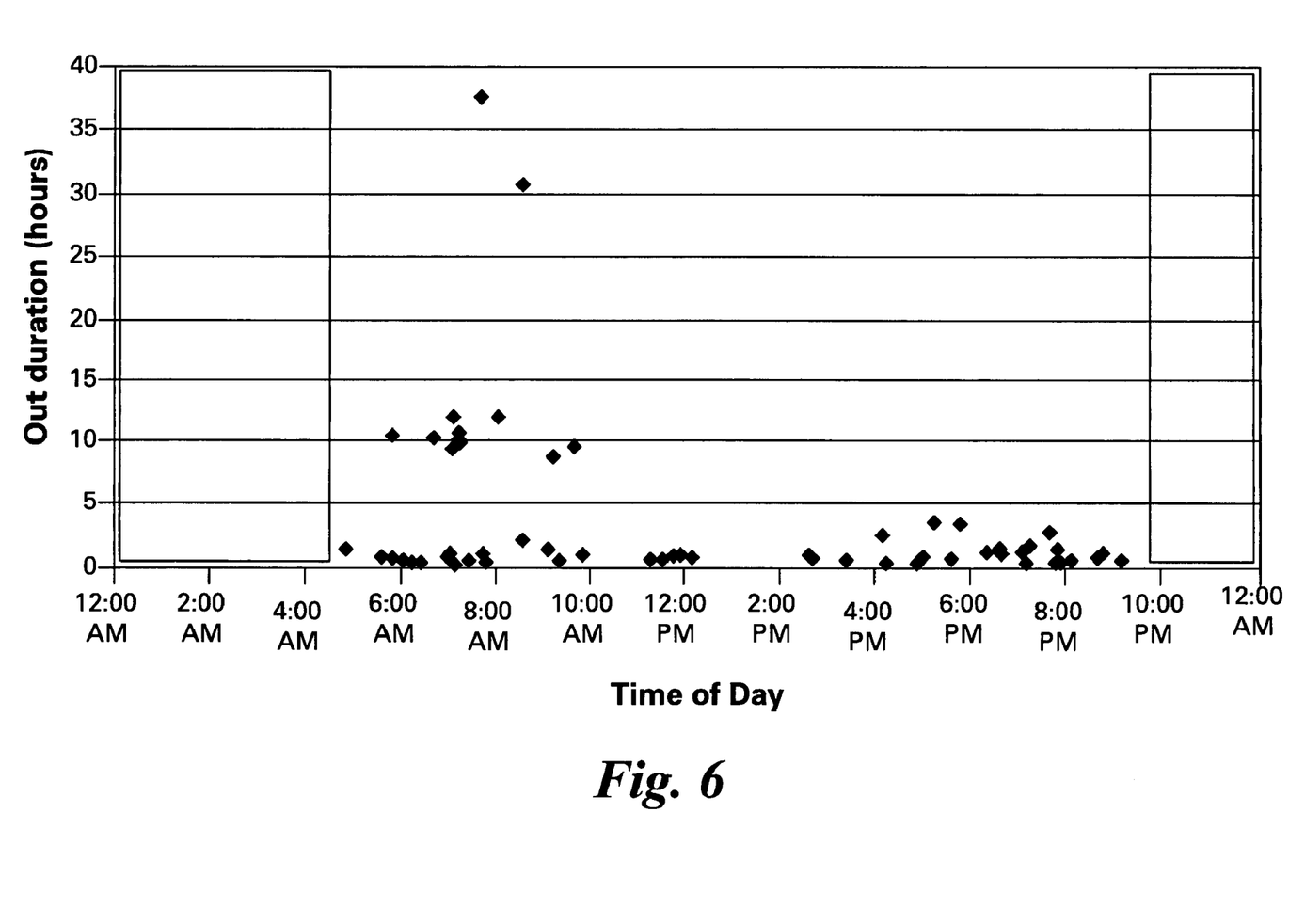
FIG. 6 is a graph illustrating clustered data points using the remote in-home monitoring system of FIG. 1.

Now with reference to FIG. 6, another exemplary method for distinguishing unusual inactivity from usual inactivity is described. Instead of constructing historical time lines, data points 19 are accumulated on a graph. An accumulation of data points 19 in a certain generalized grouping would be considered a clustering of data points 19. Thus, in the embodiment of FIG. 6, a twenty-four hour cycle is broken up into time slots, such as slots of thirty minutes or sixty minutes in duration. The data points 19 are plotted within the time slots and against the duration of the inactivity. Then, sigma limits are placed on the extreme data, the data outlying all the other data points. In this embodiment, it is advisable to obtain at least twenty data points 19 for each time slot and to collect data points 19 for between twenty and sixty days to train the system 10. Various clustering techniques can be used, such as statistical clustering and AI clustering.

Figure 7:
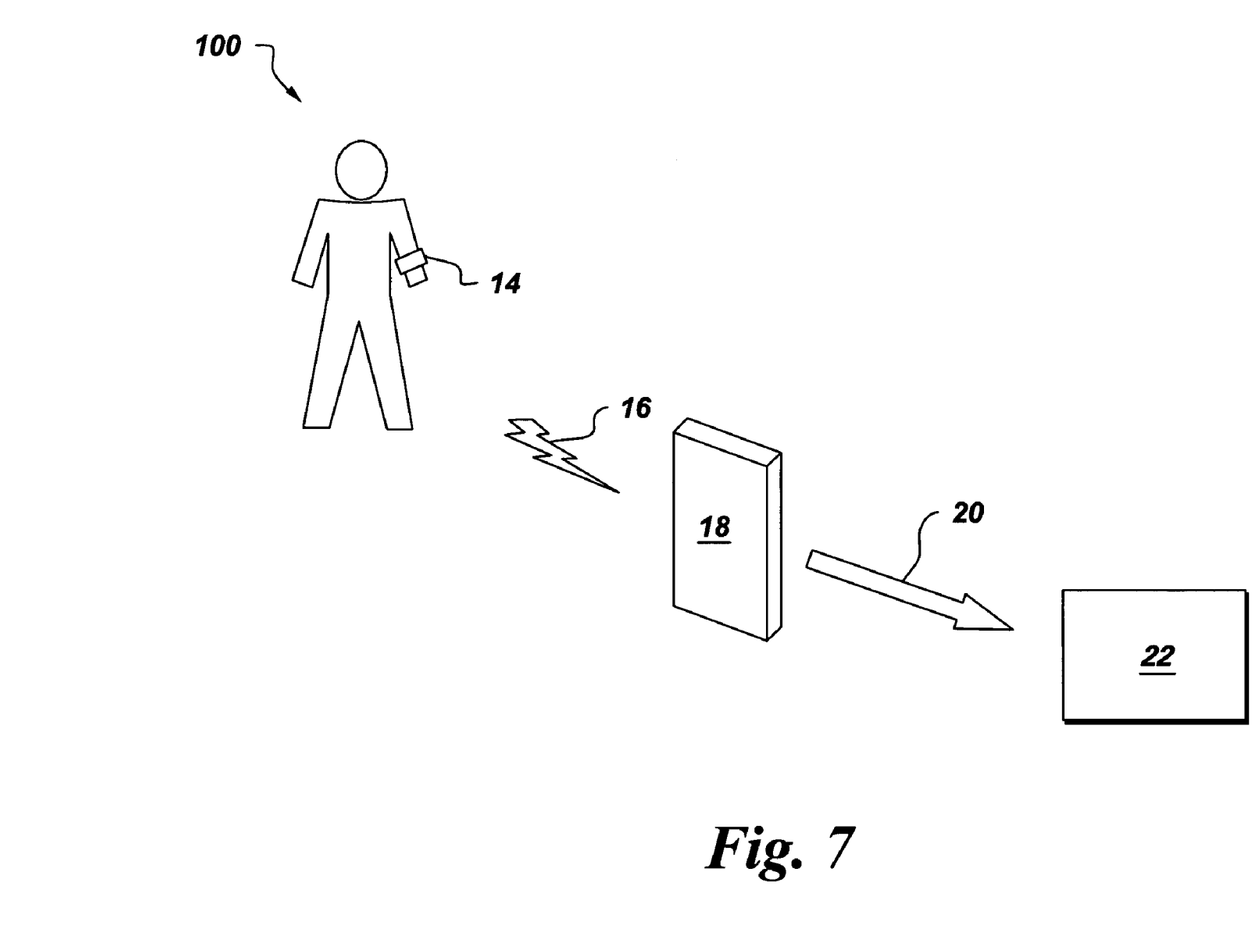
FIG. 7 illustrates an in-home monitoring system constructed in accordance with another exemplary embodiment of the invention.

Referring now to FIG. 7, there is shown an in-home monitoring system 100. The system 100 includes a single motion sensor 14 worn by the monitored resident. The activity patterns from this single sensor 14 are analyzed the same as the patterns analyzed for the system 10 described above. For example, the wearing of a single motion sensor 14 would allow an alert to be issued if the resident sat still for three hours during a time of day that, based on historical data, is when the resident is active. However, no alert would issue if the resident were inactive during a period of time that, historically, the resident is usually inactive, such as from one to four in the morning.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

What is claimed as new and desired to be protected by Letters Patent of the United States is:

1. A system for monitoring activity of a resident, comprising:
    a plurality of sensors positioned throughout a home of the resident for collecting data points on activity of the resident;
    a communication platform in communication with sensors; and
    a monitoring center located remote from the resident and in communication with the communication platform, said monitoring center comprising:
    a database for collecting the data points on activity of the resident, wherein the collected data points are collated into at least three time slots per every twenty-four hour time cycle for determining activity of the resident.

2. The system of claim 1, wherein the collected data points are collated into at least ten time slots per every twenty-four hour time cycle.

3. The system of claim 2, wherein the collected data points are collated into at least forty-eight time slots per every twenty-four hour time cycle.

4. The system of claim 1, wherein the plurality of sensors comprise one or more from the group consisting of motion sensors, exterior door sensors, inside door sensors, cabinet sensors, kitchen sensors, appliance sensors, hazard sensors, and security sensors.

5. The system of claim 1, wherein the plurality of sensors comprise at least one motion sensor and at least one exterior door sensor.

6. The system of claim 5, wherein said monitoring center is adapted to determine whether the resident is away from the home.

7. The system of claim 1, wherein said communication platform comprises a near real-time communication platform.

8. The System of claim 1, wherein at least one of the sensors is worn by the resident.

9. A system for monitoring activity within a home, comprising:
a plurality of sensors positioned throughout the home for collecting data points on activity in the home, wherein the plurality of sensors comprises one or more from the group consisting of motion sensors, exterior door sensors, inside door sensors, cabinet sensors, kitchen sensors, appliance sensors, hazard sensors, and security sensors;
a communication platform in communication with the plurality of sensors; and
a monitoring center located remote from the home and in communication with the communication platform, said monitoring center comprising:
a database for collecting the data points on activity in the home, wherein the collected data points are collated into at feast ten time slots per every twenty-four hour time cycle for determining activity Within the home.

10. The system of claim 9, wherein the collected data points are collated into at least forty-eight time slots per every twenty-four hour time cycle.

11. The system of claim 9, wherein the plurality of sensors comprise at least one motion sensor and at least one exterior door sensor.

12. The system of claim 11, wherein said monitoring center is adapted to determine whether a resident of the home is away from the home.

13. The system of claim 9, wherein said communication platform comprises a near real-time communication platform.

14. A method for distinguishing between normal and unusual activity in a home, comprising:
obtaining historical activity data within the home for a twenty-four hour cycle;
collating the historical activity data into at least three time slots within the twenty-four hour cycle; and
evaluating a new data point against the collated historical activity data to determine whether the new data point indicates normal or unusual activity in the home, wherein the activity to be distinguished is inactivity; and,
producing a maximum historical inactivity time line based upon the collated historical activity data.

15. The method of claim 14, further comprising providing a butter time to the maximum historical inactivity time line to create an alert line.

16. The method of claim 15, further comprising offsetting the buffer time, wherein the new data point is evaluated against both the historical activity data and the alert line.

17. The method of claim 15, wherein the evaluating step comprises:
collating the new data point into one of the at least three time slots; and
evaluating the new data point against the historical activity data of said one of the at least three time slots as well as against surrounding time slats.

18. The method of claim 17, wherein the evaluating step further comprises determining whether sufficient historical activity data exists for said one of the at least three time slots and for said surrounding time slots.

19. The method of claim 18, wherein the evaluating step further comprises determining whether the new data point exceeds the maximum historical inactivity time line and the alert line.

20. The method of claim 17, further comprising determining whether a resident of the home is at home or away and ignoring any new data points received during a period when the resident is away from the home.

21. The method of claim 15, further comprising creating a sleep window from the historical activity data based upon the lowest activity detected in the at least three time slots during the twenty-four hour cycle.

22. The method of claim 21, further comprising altering the alert fine within the sleep window.

23. The method of claim 14, wherein the collating step comprises collating the historical activity data into at least ten time slots within the twenty-four hour cycle.

24. The method of claim 23, wherein the collating step comprises collating the historical activity data into at least forty-eight time slots within the twenty-four hour cycle.

25. The method of claim 14, wherein the activity to be distinguished further comprises movement of an exterior door to the home.

26. The method of claim 14, wherein the activity to be distinguished further comprises activity within a kitchen in the home.

27. The method of claim 14, wherein the evaluating step includes plotting the new data point against the collated historical activity data to determine whether the new data point indicates normal or unusual activity in the home.

28. A method for distinguishing between unusual periods of inactivity and normal periods of inactivity in a home, comprising:
obtaining historical activity data within the home for a twenty-four hour cycle;
collating the historical activity data into at least ten time slots within the twenty-four hour cycle;
producing a maximum historical inactivity time line based upon the collated historical activity data; and
evaluating a new data point against the collated historical activity data to determine whether the new data point indicates an unusual period of inactivity or a normal period of inactivity in the home.

29. The method of claim 28, further comprising providing a buffer time to the maximum historical inactivity time line to create an alert line.

30. The method of claim 29, further comprising offsetting the buffer time, wherein the new data point is evaluated against both the historical activity data and the alert line.

31. The method of claim 29, wherein the evaluating step comprises:
collating the new data point into one of the at least three time slots; and evaluating the new data point against the historical activity data of said one of the at least three time slots as well as against surrounding time slots.

32. The method of claim 31, wherein the evaluating step further comprises determining whether sufficient historical activity data exists for said one of the at least three time slots and for said surrounding time slots.

33. The method of claim 32, wherein the evaluating step further comprises determining whether the new data point exceeds the maximum historical inactivity time line and the area line.

34. The method of claim 33, further comprising issuing an alert when the new data point exceeds the maximum historical inactivity time line and the alert line.

35. The method of claim 29, further comprising creating a sleep window from the historical activity data based upon the lowest activity detected in the at least three time slots during the twenty-four hour cycle.

36. The method of claim 35, further comprising altering the alert line within the sleep window.

37. The method of claim 36, wherein the evaluating step further comprises determining whether the new data point exceeds the maximum historical inactivity time line and the alert line.

38. The method of claim 37, further comprising triggering an alert and delaying issuance of the alert until after the sleep window has elapsed.

39. The method of claim 37, further comprising triggering an alert and e-mailing the alert to a caregiver.

40. The method of claim 29, further comprising determining whether a resident of the home is at home or away and ignoring any new data points received during a period when the resident is away from the home.

41. The method of claim 29, wherein the collating step comprises collating the historical activity data into at least ten time slots within the twenty-four hour cycle.

42. The method of claim 41, wherein the collating step comprises collating the historical activity data into at least forty-eight time slots within the twenty-four hour cycle.

* * * * *